United States Patent [19]

Simkiss et al.

[11] Patent Number: 5,258,307
[45] Date of Patent: Nov. 2, 1993

[54] SINGLE STAGE AVIAN EMBRYO CULTURE PROCESS

[75] Inventors: Kenneth Simkiss, Reading, England; Roy G. Smith, Westfield, N.J.

[73] Assignee: Merck & Co., Inc., Rahway, N.J.

[21] Appl. No.: 583,424

[22] Filed: Sep. 17, 1990

[51] Int. Cl.$^5$ .................. C12N 5/00; A01K 67/00
[52] U.S. Cl. .................. 435/317.1; 435/240.2; 800/2; 800/DIG. 6; 119/6.8
[58] Field of Search .................. 800/2, DIG. 6; 435/240.2, 317.1; 119/68

[56] References Cited

FOREIGN PATENT DOCUMENTS 295964 6/1988 European Pat. Off. .

OTHER PUBLICATIONS

Dunn and Boone, Poultry Sci. 55: 1067–1071 (1976).
Dunn and Boone, Poultry Sci. 57: 370–377 (1977).
Ono and Wakasugi, Poultry Sci. 63: 159–166 (1984).
Rowlett and Simkiss, British Poultry Sci. 38: 91–101 (1987).
Perry, J. Anat. 150: 99–109 (1987).
Kochav et al, Dev. Biol. 79: 296–308 (1980).
Perry, Nature 331: 70–71 (1988).
Naito et al, J. Exp. Zool. 254: 322–323 (1990).
Mongin and Sauveur, C. R. Acad. Sci. Paris 270 D. 1715–1718 (1970).
New, J. Embroye, Exp. Morpho. 5: 293–299 (1957).
Demming et al, J. Exp. Zoo. Supp. 1: 341–345 (1987).

*Primary Examiner*—Jasemine C. Chambers
*Attorney, Agent, or Firm*—Christine E. Carty; Jack L. Tribble; Hesna J. Pfeiffer

[57] ABSTRACT

A novel single stage culture system for avian embryos is disclosed. Premature eggs consisting of about 32 to about 100 cells are collected shortly after ovulation and prepared for culture. The eggs are incubated in a potassium rich bicarbonate solution and the contents of the eggs are transferred to recipient eggshells. The open end of the eggshell is closed and the embryos are turned and incubated in an oxygen enriched atmosphere for about 3–4 days. For the final incubation period the eggs are incubated in an upright position and rocked hourly.

4 Claims, 2 Drawing Sheets

SINGLE STAGE AVIAN EMBRYO CULTURE PROCESS

BACKGROUND OF THE INVENTION

In vitro culturing techniques have been used to evaluate the chemistry and physiology of avian development and morphogenesis. Initial techniques were developed for the culturing of 3 day fowl embryos in plastic containers, Dunn and Boon, Poultry Sci. 55: 1067-1071 (1976) and Dunn and Boone, Poultry Sci. 57: 370-377 (1977). The method permits extensive embryonic development but the culture process does not produce viable hatchlings because the embryos show retarded growth and become progressively hypocalcemic. The results of in vitro embryo culture have been improved by culturing embryos in contact with eggshells from which they are able to resorb calcium, Ono and Wakasugi, Poultry Sci. 63: 159-166 (1984). The success of the above techniques has been improved by rocking the surrogate eggshells to produce normal hatchlings, Rowlett and Simkiss, British Poultry Sci. 28:91-101 (1987).

Genetic manipulation of avian primordial germ cells requires a culturing system which will allow the culturing of embryos much smaller than those three days of age. Fertilization (gamete interaction) generally takes place within 15 min of ovulation, with the first cleavage division taking place about 4 hr later, Perry, J. Anat. 150: 99-109 (1987). The ovum begins passage through the oviduct and is invested with albumen in the magnum and with the shell membrane in the isthmus where cleavage commences. Following the first cleavage the cells continue to divide giving rise to a simple sheet of cells overlying a subblastodermal cavity (Kochav et al., Dev. Biol. 79:296-308 (1980). As the soft-shelled egg moves from the oviduct to the uterus the albumen is doubled and the shell undergoes slow calcification. Embryonic morphogenesis and growth take place during the next 21 days and result in fully developed and viable bird that is capable of hatching.

The initial attempt at culturing embryos younger than 3 days was by Perry, Nature 331: 70-71 (1988) and Perry, European Patent Publication No. 295,964, published Dec. 21, (1988). The Perry process requires that the artificially inseminated hens be sacrificed at 2.75 hr after the preceding egg was laid to obtain the fertilized ova. The ova are placed in glass jars and a culture medium was added (culture system I). The culture medium consisted of liquid albumen collected form freshly laid eggs (3 parts) and a salt solution (2 parts) containing (50 mmole $KHCO_3$, 30 mmole $NaHCO_3$, 10 mmole KCl, 2.5 mmole $MgCl_2.6H_2O$, 0.7 mmole $CaCl_2.2H_2O$ and 11 mmole glucose. The pH was lowered from an initial value of 8.4 to 7.2-7.4 by stirring in an atmosphere of $CO_2$. The jars were sealed with Saran Wrap incubated at 41°-42° C. for 24 h. Following incubation the contents of the jars were transferred to recipient egg shells and the shells filled with medium (liquid albumen, 2 parts; salt solution, 1 part), pH 8.2-8.4 and sealed with cling film (culture system II). The eggs of culture system II were rocked intermittently through an angle of 90° in hourly cycles at 38° C., relative humidity (RH) 40-50% for 3 to 6 days. The contents of culture system II are transferred to larger eggshells and the shells are sealed (culture system III). The cultures were incubated at 38° C., RH 40-60% and rocked intermittently through an angle of 30° in hourly cycles for 5 days, then maintained in a stationary position for the remaining period. The temperature was lowered by 2° C. for the final 3 days. Perforations were made in the cling film cover at 1-2 days before hatching and the cling film was replaced with a lid 12 h before hatching.

Perry's three stage system for the culture of oviducal eggs attempts to mimic the dynamic water and ion fluxes that occur in the shell gland of the fowl during the last 20 h of egg formation. This appears to have been done without an understanding of the critical physiological events that take place during this period of egg formation in fowl. The excessive transfer of the embryos and the limited understanding of the appropriate physiological events resulted in a very low level of successful hatchings by the Perry culture system. This system has been improved by Naito et al., J. Exp. Zool. 254: 322-328 (1990), who completely replaced the thick albumen of the individual eggs with thin albumen and obtained a hatch rate of 34.4%.

OBJECTS OF THE INVENTION

It is, accordingly, an object of the present invention to provide a method for gaining easy access to the first few cells in avian development. A further object is to provide an understanding of the critical physiological events that happen during the final 20 h of egg formation in fowl and to apply this to a successful culture system. Another object is to provide a simplified in vitro culture system that enables premature softshelled eggs to be cultured to produce viable chicks. A further object is to provide an in vitro culture system that enables genetic manipulation of the fertilized ovum. Another object is to provide an in vitro culture system which will allow the introduction of foreign DNA into germ line cells resulting in transgenic fowl. A further object is to provide an in vitro culture system that will allow the introduction of genes for novel proteins into the germ line and result in the expression of the proteins in egg white.

SUMMARY OF THE INVENTION

A novel single stage culture system for avian embryos is disclosed. Premature eggs consisting of about 32 to about 100 cells are collected shortly after ovulation and prepared for culture. The eggs are incubated in a potassium rich bicarbonate solution and the contents of the eggs are transferred to recipient eggshells. The open end of the eggshell is closed and the embryos are turned and incubated in an oxygen enriched atmosphere for about 3-4 days. For the final incubation period the eggs are incubated in an upright position and rocked hourly.

DETAILED DESCRIPTION OF THE INVENTION

Figure 1A:
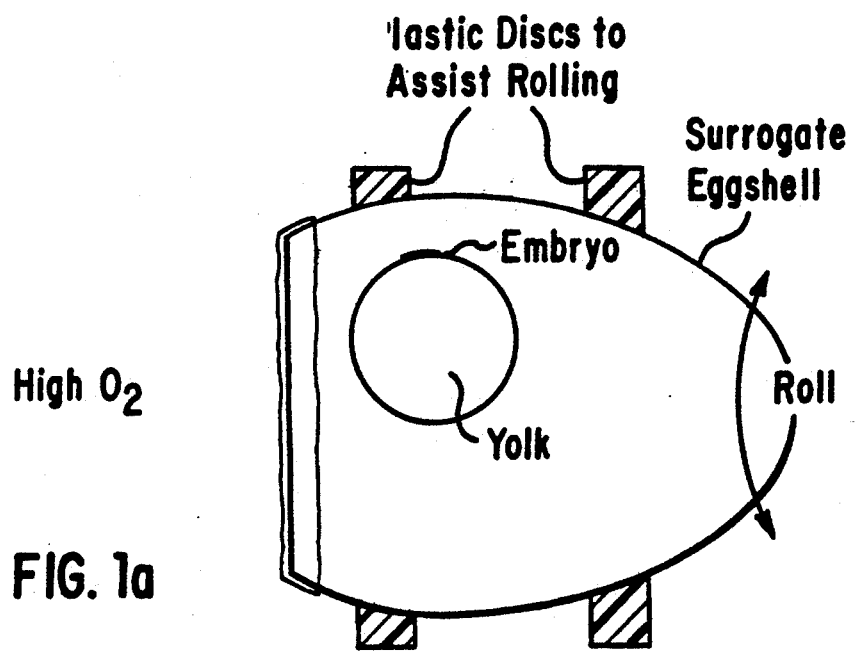
FIGS. 1a and 1b. Culture system.

The present invention relates to a simplified in vitro culture system that enables premature soft-shelled eggs to be cultured to produce viable chicks. Premature fertilized soft-shelled eggs are collected at about 4 to about 9 hours after ovulation from fowl by hormone treatment or by mechanical means. Fowl is defined herein as wild or domesticated gallinaceous birds that serve as a source of meat or eggs and that include, but are not limited to, commercially important birds such as chickens, turkeys, ducks, geese, guinea fowl, pheasants, pigeons, peafowl and quail. Fowl as used herein will also include poultry, defined as all domesticated birds kept for meat. The preferred methods of collecting the premature softshelled eggs is by the injection of vasopressin or similarly acting compound at about 4 to about 9 h after ovulation, preferably about 6 to about 7 hours, or by gentle external pressure on the abdomen anterior to the shell gland at the same time periods. If vasopressin is used the concentration will range from about 0.5 U to 3 U with about 1 to about 2 U being preferred. The eggs are collected at this time to assure that limited cell divisions have occurred. The first cell divisions normally occur at about 5 to 6 h after fertilization when the egg is leaving the isthmus region and entering the shell gland of the oviduct. Embryos collected between 5 and 6 h will generally consist of about 32 to about 100 cells. Embryos containing fewer cells, about 2 to about 16, are obtained by collecting the softshelled eggs at about 4 to about 5 h after fertilization. All manipulations of the soft-shelled eggs and embryos are carried out under aseptic conditions.

Initial attempts at in vitro embryo culture of about 2 to about 100 cells have identified three problems that had to be overcome before successful culturing could be routinely carried out. An understanding of these problems resulted in the present invention. First, the albumen that is initially secreted around the ovum has a Na/K ratio of about 10:1 moles. It is a remarkable fact that this albumen is incompatible with embryonic growth and must be modified to a ratio of about 2:1 Na/K before development can proceed. This change normally occurs during the 20 hours taken for shell formation. Second, the embryo that develops in culture is initially very vulnerable to dehydration. An extra embryonic membrane, the anmion, develops by day 3 and protects the embryo. Prior to the development of the amnion the embryo needs to be kept at saturation humidity. Third, early growth of the cultured embryo is enhanced by a slight increase in oxygen of about 2% to about 7%, with about 5% being preferred.

Devising a suitable incubation solution and conditions to overcome the three problems associated with early embryo in vitro culture has been difficult and this may have been one of the reasons Perry ended up with a three stage culture system. Changing the composition of the solution can lead to direct osmotic swelling. In addition ionic changes produce Donnan equilibrium effects that also induce osmotic swelling. The swelling can be detrimental to normal embryo development. The egg nominally takes up both ions and liquid albumen and the incubation solution needs to simulate tins in a static state whereas in the bird these processes are normally driven by continual ion fluxes in the oviduct.

A critical aspect of the invention requires a change in the Na/K molar ratio of the albumen prior to oviducal egg incubation. The shift in the molar ratio is generally accomplished in a dynamic system by dialysing the soft-shelled egg for about 15 to about 30 hours, with about 20 to 24 h preferred, before explanting the egg into a surrogate eggshell. The dialysis may be carried out with or without movement of the soft- shelled eggs in the albumen medium. The premature oviducal eggs are placed in various saline solutions with K:Na molar ratios of from about 2:1 to about 7:1 using either $HPO_4$ or $HCO_3$ as buffering ions. Total concentrations ranged from about 160 to about 250 ion equivalents per liter. Saline solutions are mixed with thin albumen in ratios of from about 1:1 to about 1:2.3. The thin albumen is collected from fresh laid eggs. The premature eggs, are rotated at speeds of from about 0.5 to about 3 revolutions per min, with about 1 to about 2 revolutions per min being preferred, at about 38° C. for periods of about 6 to 30 h, with about 20 to 24 h being preferred. Dialyzed eggs and control eggs are used for Na and K analysis using flame photometry. Phosphate buffered salines are less effective than bicarbonate in maintaining subsequent development. Successful incubation to hatching is obtained with a solution consisting of about 1 L containing about 300 ml of about 60 mmole/L $KHCO_3$, about 30 mmole/L NaCl, about 11 mmole glucose and about 700 ml thin albumen. The saline solution can be used with or without antibiotics. If antibiotics are used it is recommended that about 6 mg penicillin, about 50 mg streptomycin be added to about 1 L of the solution.

It has been shown by Mongin and Sauveur, C.R. Acad. Sci. Paris 270D, 1715-1718 (1970), that the sodium content of the albumen decreases from about 140 mmole/L at the start of shell formation to about 50 mmole/L shortly before oviposition while the potassium levels rise from about 13 mmole/L to 60 mmole/L over the same period. These changes appear to be responsible for the equivalent changes in albumen which passed from a composition with a Na:K ratio of about 10.2 at the start of shell formation to one of about 2.5 shortly before oviposition. If it is assumed that the premature eggs each contain about 30 g albumen a complete equilibration between the eggs and the incubation solution would produce a sodium concentration of about 97 mmole/L and a potassium concentration of about 37 mmole/L, which is very close to the composition of a normal, new laid egg. Analysis of premature eggs in the solution of this invention show that the albumen came close to these equilibrium values in about 6 h.

Dialysis resulting in the appropriate albumen concentration and the appropriate Na:K ratio of the soft shelled eggs is carried out in any appropriately sealed container. Preferably the container will maintain a constant environment with respect to atmospheric and ionic conditions. The ratio of eggs to dialysis fluid will vary with the size of the eggs. It is preferred that Rhode Island Red soft- shelled eggs be dialyzed at a ratio of about 1 to about 6 eggs per 100 ml of the dialysis fluid.

Figure 1B:
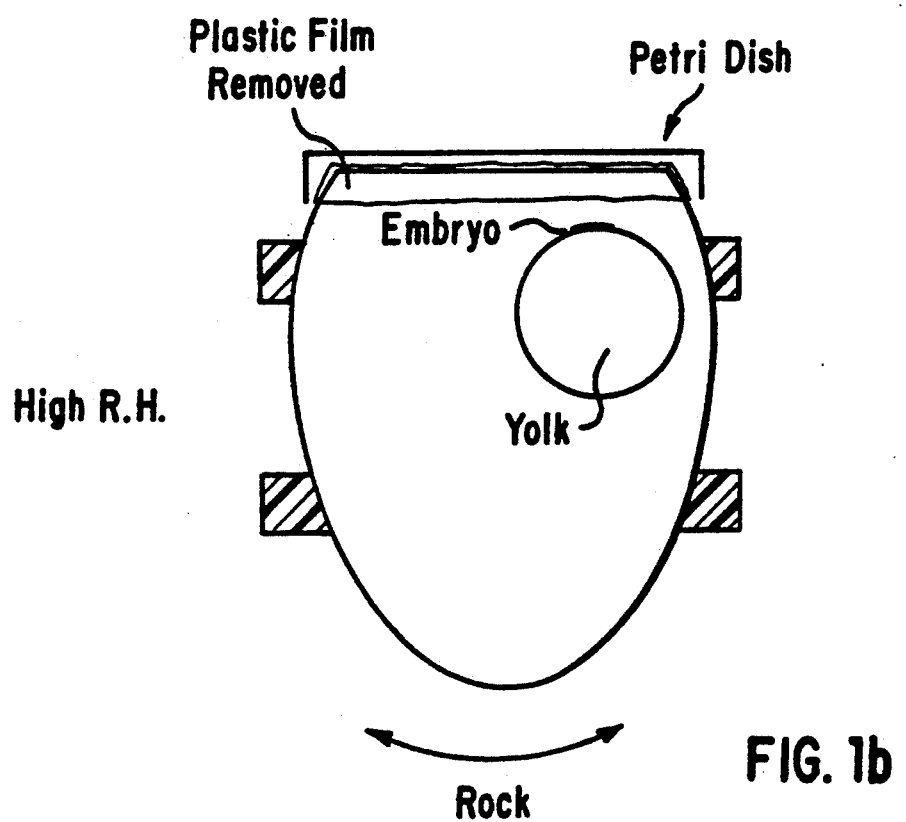

It has been shown previously (New, J. Embryol. Exp, Morpho. 5: 293-299 [1957]; Damming et al., J. Exp. Zoo. Supp. 1:341-345 [1987]) that is important to turn eggs during the first week of incubation. This is best accomplished by sealing the egg contents into a surrogate eggshell that could be turned normally. The dialyzed eggs are transferred to surrogate eggshells, that have been swabbed externally with an antiseptic. The soft shelled eggs are removed from the dialysis solution, the shell membrane cut and the contents transferred to the surrogate eggshells. The open end of the eggshell is surrounded with double-sided adhesive tape such as that produced by Copydex and the egg is sealed with plastic wrap, see FIG. 1. The plastic wrap may include, but is not limited to, a low gaseous permeability plastic wrap such as Saran Wrap (Dow Chemical) or partially gas permeable plastic wraps that do not contain PVC additives. The enclosed embryos are incubated on their side in an incubator with a nominal turning mechanism and automatic control over temperature, oxygen, carbon dioxide and relative humidity. For about the first 3 days the eggs are kept at about 37.5° C. in an atmosphere with about 80% relative humidity and about 25% oxygen.

After the initial incubation phase the eggs are end, the plastic wrap is perforated and covered with a loose fitting cover, such as a petri dish. The incubation is continue 21% oxygen until the day before hatching. At about 24 h before hatching the carbon dioxide level of the incubator is raised to 2% and the fowl are allowed to hatch.

The problem of embryo dehydration is solved by enclosing the embryos in surrogate eggshells and sealing the opening with plastic wrap. While this maintains the egg contents in a high humidity environment it may reduce the availability of oxygen. The potential oxygen deprivation is corrected with about a 4% increase in oxygen levels maintained during the first few days of culturing.

As discussed above the methods of this invention will be suitable for culturing embryos smaller than 32 cells and for genetic manipulation of the smaller embryos. Indeed, this invention would be suitable for retroviral or liposomal infection of the about 2-8 cell embryo through the shell membrane prior to dialysis. If micro injection of the nucleus is required it would obviously be necessary to remove the shell membrane and reseal the egg in a dialysis membrane to complete the ion exchange process. An alterative would be to replace completely the albumin solutions and go straight into an eggshell.

The following examples illustrate the present invention without, however, limiting the same thereto.

EXAMPLE 1

Evaluation of Incubation Conditions

Figure 2:
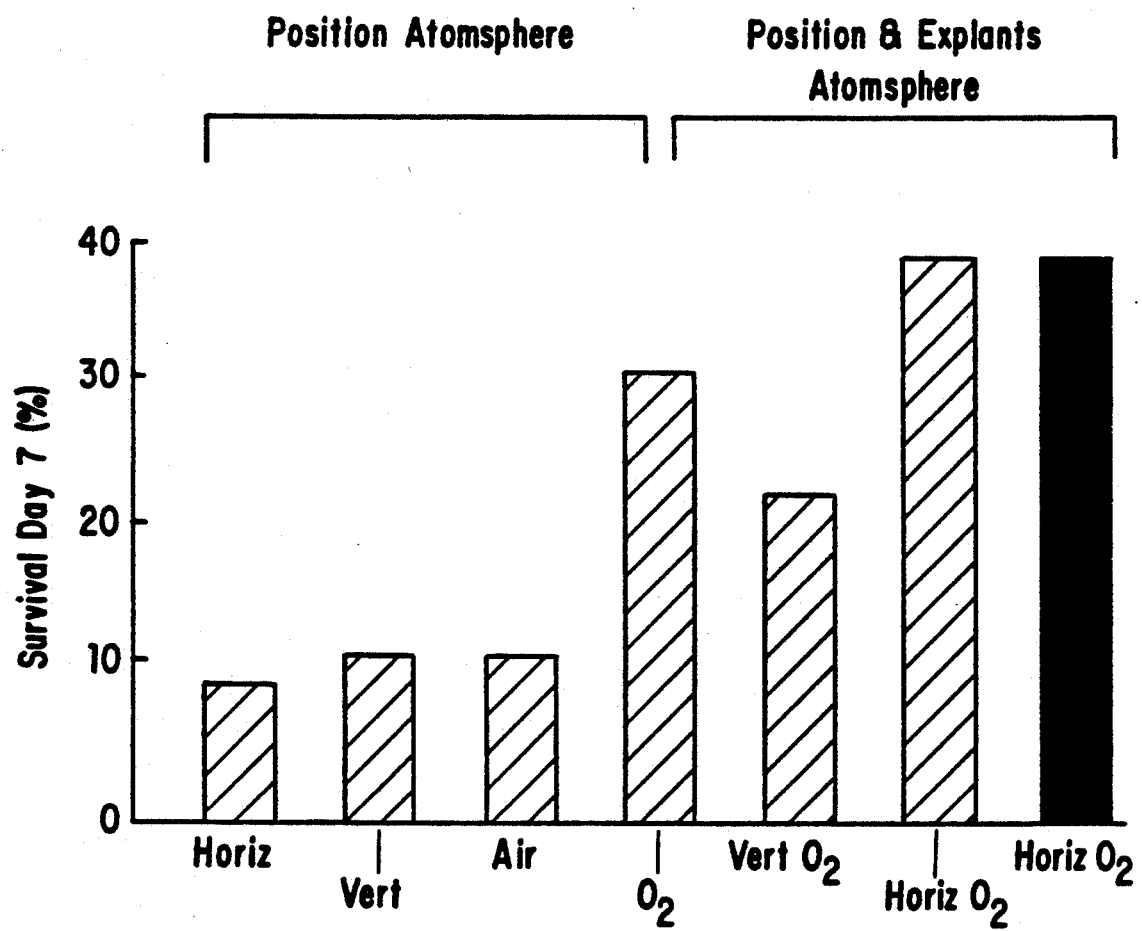
FIG. 2. Effect of oxygen on cultured embryos.

Previous studies by New, J. Embryol. Exp, Morpho. 5: 293-299 (1957) and Damming et al., J. Exp. Zoo. Supp. 1:341-345 (1987), have shown that it is important to turn eggs during the first week of incubation. It was therefore decided that the egg contents would benefit from being sealed into a surrogate eggshell that could be turned normally. Preliminary experiments were undertaken to evaluate the effect of removing the top from the blunt end of normal eggs and resealing them with "clingfilm" attached to the eggshell with double-sided tape (Copydex). Such eggs were incubated vertically or horizontally in normal air or in air enriched to give 25% oxygen. Similar experiments were undertaken with unincubated fertile eggs that were transferred from their original shell to a surrogate eggshell. The survival of normal fertile eggs that had been opened and sealed with "clingfilm" is shown in FIG. 2. The effect of oxygen is clearly shown in increasing the numbers of embryos developing to day 7. Explanting day 0 eggs into surrogate eggshells gave similar rates of successful incubation, see FIG. 2.

EXAMPLE 2

Isolation And Dialysis Of Oviducal Eggs

Premature eggs were collected from a laying flock of Rhode Island Red "strain" fowl by injecting 1-2 i.u. vasopressin 6 to 7 hr after ovulation. Alternatively the eggs were expressed by gentle external pressure on the abdomen anterior to the shell gland. The oviducal eggs collected in this manner were placed in various saline solutions with K:Na molar ratios of from 2:1 to 7:1 using either HPO$_4$ or HCO$_3$ as buffering ions. Total concentrations ranged from 160 to 250 ion equivalents per liter. Saline solutions were mixed with thin albumen in ratios of from 1:1 to 1:2.3. From 10 to 14 eggs were placed in these solutions in a sealed jar and rotated at speeds of from 1 to 2 revolutions per minute at 38° C. for periods of 20 to 24 h. Eggs were weighed before and after being dialysed in such solutions. Premature eggs before and after this dialysis treatment were used for Na and K analyses using flame photometry.

Dialysing premature oviducal eggs in solutions with K:Na ratios of 2:1 gave approximately 25% survival at day 3. Subsequent survival in surrogate eggshells was similar to that found by Rowlett and Simkiss, British Poultry Sci. 28: 91-101 (1987) or about 21%. Phosphate buffered salines were less effective than bicarbonates in maintaining subsequent development. Premature eggs were quite variable in the extent to which they changed weight during dialysis, with the typical values being from +8 to −2 g. Successful incubation to hatching was obtained with a solution consisting of 1 L containing 300 ml of 60 mmole/L KHCO3, 30 mmole/L NACL, 11 mmole glucose, 6 mg penicillin, 50 mg streptomycin and 700 ml thin albumen.

EXAMPLE 3

Incubation of Dialysed Eggs

The dialyzed soft shelled eggs from Example 2 were transferred to surrogate eggshells, that had been swabbed externally with 70% alcohol and a portion of the shell at the large end of the egg was removed. After 20-24 hr the soft shelled eggs are removed from the solution, the shell membrane is cut and the contents transferred to the recipient eggshells. The open end of the eggshell is surrounded with double-sided adhesive tape and the egg is sealed with a cling-film plastic sheet. The eggs are continuously turned and incubated at 37° C. with 70 to 80% relative humidity in an oxygen enriched atmosphere (25% oxygen) for 3-4 days. After this initial phase the eggs were placed in an upright position and rocked hourly. At this time the clingfilm cover was perforated, covered with a loose fitting petri dish and incubation continued in an environment containing 21% oxygen. On the day before hatching was due the carbon dioxide level of the incubator was raised to 2%.

What is claimed is:

1. A process for the in vitro culture of fertilized fowl embryos consisting essentially of:
   (a) collecting premature fertilized soft-shelled fowl eggs containing about 100 or fewer cells;
   (b) placing the soft-shelled eggs in a dialysis solution, the dialysis solution being contained in a sealable container, and the dialysis solution containing about 18 mM potassium, about 9 mM sodium, bicarbonate and thin albumen;
   (c) sealing the container;
   (d) incubating the soft-shelled eggs at about 38° C. for between about 6 hours and about 30 hours and at between about 0.5 and about 3 rpm to produce dialyzed eggs containing about 97 mmole/L sodium and about 37 mmole/L potassium;
   (e) transferring the contents of the dialyzed eggs to a surrogate eggshell;
   (f) incubating at between about 35° C. and about 38° C. in an oxygen enriched environment containing about 25% oxygen until about 24 hours prior to hatching; and (g) allowing hatching to occur.

2. The in vitro process of claim 1 wherein the premature fertilized soft-shelled fowl eggs contain between 2 and 64 cells.

3. The in vitro process of claim 2 wherein the dialysis solution comprises about 300 mL of about 18 mM $KHCO_3$, about 10 mM NaCL, about 3.3 mM glucose, about 6 mg penicillin, about 50 mg streptomycin and about 700 mL thin albumen.

4. The process of claim 1 in which a dialysis step results in a premature fertilized egg having a sodium concentration of about 97 mmole/L and a potassium concentration of about 37 mmole/L.

* * * * *